United States Patent [19]

Kardos et al.

[11] Patent Number: 4,528,131
[45] Date of Patent: Jul. 9, 1985

[54] PROCESS AND PREPARATION FOR THE QUANTITATIVE DETERMINATION OF SUBSTANCES ABLE TO BIND TO CEREBRAL RECEPTORS AND A PROCESS FOR PREPARING THE PREPARATION

[75] Inventors: Julianna Kardos; Gábor Maksay; Miklós Simonyi, all of Budapest, Hungary

[73] Assignee: MTA Központi Kémiai Kutató Intézet, Budapest, Hungary

[21] Appl. No.: 470,043

[22] Filed: Feb. 28, 1983

[51] Int. Cl.$^3$ .................... C07G 7/00; G01N 33/58; G01N 33/60
[52] U.S. Cl. ............................ 260/112 R; 436/503; 436/504; 436/545; 436/547; 436/804; 436/815
[58] Field of Search ............ 436/503, 504, 545, 547, 436/804, 815; 260/112 R

[56] References Cited

PUBLICATIONS

Sigel et al., J. Biological Chemistry, 258 (1983), 6965–6971.
Enna et al., Chemical Abstracts, 84 (1976) #39778u.
Mackerer et al., J. Pharmacol. Exp. Ther., 206 (1978), 405–413.

Primary Examiner—Christine M. Nucker
Attorney, Agent, or Firm—Keil & Weinkauf

[57] ABSTRACT

A process for preparing a stable receptor preparation suitable for the quantitative determination of substances able to bind to cerebral receptors in which a brain or brain-region material is homogenized with an aqueous solution of an inert substance soluble in water; the formed homogenizate is centrifuged at an acceleration of 800 to 110 g for 8 to 20 minutes to form a supernatant; the brain or brain-region material is isolated from the supernatant by centrifuging the supernatant at an acceleration of 18,000 to 22,000 g for 10 to 20 minutes, the thus-obtained solid substance is rehomogenized in distilled water; the homogenizate is frozen and then thawed and thereafter centrifuged at an acceleration of 7000 to 9000 g for 5–15 minutes; the supernatant is isolated, centrifuged at an acceleration of 35,000 to 45,000 g for 20 to 30 minutes; the obtained solid substance is washed with an aqueous buffer solution of a pH value between 6 and 8, and a suspension consisting of the solid substance and the washing liquid is frozen and then thawed at least once and thereafter the suspension is lyophilized.

8 Claims, No Drawings

PROCESS AND PREPARATION FOR THE QUANTITATIVE DETERMINATION OF SUBSTANCES ABLE TO BIND TO CEREBRAL RECEPTORS AND A PROCESS FOR PREPARING THE PREPARATION

The invention relates to a process and a preparation for the quantitative determination of substances able to bind to cerebral receptors (first of all benzodiazepines, β-adrenergic blocking substances and γ-amino-butyric acid). Furthermore, the invention relates to a process for preparing the preparation used in the determination.

In therapeutics it is often necessary for diagnostic and/or therapeutic purposes to determine the quantity of substances in the body fluids that are binding to cerebral receptors. Thus, from the content of γ-amino-butyric acid of the spinal fluid conclusions can be drawn for certain cerebral diseases.

It is also known that the body fluids contain the substance to be determined in a very low ($10^{-8}$ to $10^{-12}$ mole) concentration, thus their quantitative measurement demands special sensitive methods.

Mass spectrometric, high-capacity liquid-chromatographic and ion-exchange fluorometric methods suitable for the determination of the quantity of γ-amino-butyric acid are described in the following publications: J. Chromat. 118, 395 (1976), Brain Res. 167, 297 (1979) and Anal. Biochemistry 101, 349 (1980). Though these methods are sufficiently sensitive, their common disadvantage resides in the fact that the biological sample to be examined cannot be directly used in the measurement but only after elaborate sample preparation (purification in several steps, derivative preparation etc.).

For performing the radioreceptor test recently described for the quantitative determination of γ-amino-butyric acid [J. Neurochem. 28, 1121 (1977); Brain Res. 182, 99 (1980); Clinica Chimica Acta 109, 77 (1981)] no preparation of the body fluid to be examined is necessary. It is disadvantageous, however, that the receptor suspension necessary for performing the test has to be freshly prepared from the brain of test animals. For this purpose it is necessary to maintain an animal house and a special biochemical laboratory which the hospitals and clinics generally do not possess. Thus, a receptor preparation is necessary which can be stored in dry state for unlimited time and can be reliably used for the quantitative determination of substances binding to cerebral receptors.

The published German patent application No. 2,902,071 discloses the preparation of a simply treatable and unlimitedly storable dry receptor preparation. According to this method the receptor compound is prepared by homogenizing the animal brain-tissue in an aqueous solution of a neutral, water-soluble substance—suitably saccharose—and by freeze-drying the homogenizate.

The disadvantage of the known receptor preparation is, however, that it can only be used for the quantitative determination of benzodiazepines and it is not suitable for the separate measurement of benzodiazepine receptors of different types. The quantitative determination of other substances binding to cerebral receptors, such as γ-amino-butyric acid and β-adrenergic blockers, is not possible with the known receptor preparation.

In the course of our examinations it has been observed that this deficiency can be attributed to the fact that the known receptor preparation contains the predominant part of the cerebral receptors in a form inactivated by endogeneous substances. We have discovered that by the complete removal of the inactivating endogeneous substances the cerebral receptor sites can be set free, thus the preparation becomes suitable for the determination of every substance which can bind to cerebral receptors.

Based on the above discovery the invention relates to a process for preparing a stable receptor preparation suitable for the quantitative determination of substances binding to cerebral receptors. According to the invention one proceeds in the following way: a brain or brain-region homogenizate prepared with the aqueous solution of an inert substance soluble in water is centrifuged at an acceleration of 800 to 1100 g for 8 to 20 minutes, the supernatant is isolated and centrifuged at an acceleration of 18,000 to 22,000 g for 10 to 20 minutes, the thus-obtained solid substance is again homogenized in distilled water, then, if desired, the homogenizate is frozen and thawed and thereafter centrifuged at an acceleration of 35,000 to 45,000 g for 20 to 30 minutes, the obtained solid substance is washed at least once with an aqueous buffer solution of a pH-value between 6 and 8, while washing the suspension consisting of the solid substance and the washing liquid is, if desired, frozen and thawed at least once, and finally the suspension is lyophilized.

By this process a solid, stable, unlimitedly storable receptor preparation is obtained which contains the cerebral receptor site in active state and which can be generally used in radioreceptor tests for the quantitative determination of substances which are able to bind these cerebral receptor sites.

It is suitable to use animal (rat, bovine, chicken etc.) brains as starting substance from which the brain homogenizate is prepared in the way described in published German patent application No. 2,902,071. Suitably, saccharose is added to the aqueous medium as the water-soluble inert substance. By the first centrifugation performed at an acceleration of 800 to 1100 g the rough deposit is isolated from the brain or brain-region homogenizate; the supernatant that is obtained contains the basic substance of the receptor preparation. From the supernatant the basic substance of the receptor preparation is isolated in a state contaminated by nuclei of the cell and mitochondrium by the second centrifuging step performed at an acceleration of 18,000 to 22,000 g. In this step the basic substance of the receptor preparation contains the predominant majority of the receptor sites still in a state inactivated by endogenous substances. Then this solid substance is again homogenized in distilled water whereby the cell membranes burst open and the endogenous substances blocking the active receptor sites get into the aqueous medium. The rehomogenization is suitably performed in cold (4° to 10° C.) distilled water. For the rehomogenization of 1 part by weight of a solid substance suitably at least 15 parts by weight of distilled water are used. It can be generally stated that the more distilled water that is used for the rehomogenization, the more efficiently the blocking endogenous substance can be removed from the active receptor sites. The upper limit of the quantity of the distilled water is determined essentially by economical factors. For the rehomogenization of 1 part by weight of a solid substance usually 10 to 20 parts by weight of distilled water are used.

In order to promote the bursting open of the cell membranes, if desired, the distilled aqueous homogenizate can be frozen and then thawed.

By the first centrifugation performed at an acceleration of 7000–9000 g, from the distilled aqueous homogenizate the cell nuclei and mitochondria are eliminated, which contain no active receptor sites and the presence of which could disadvantageously influence the properties (e.g. filterability) of the receptor preparation. By the following centrifuging step performed at an acceleration of 35,000 to 45,000 g the basic substance of the preparation is isolated from the supernatant, whereafter this substance is washed at least once with an aqueous buffer solution of a pH-value between 6 and 8, preferably with a tris-citrate buffer solution (pH=7.1). The efficiency of the purification can be increased by freezing and thawing at least once the suspension consisting of the washing liquid and the solid substance in the course of the washing. If washing is carried out only once, the washing liquid is removed and the obtained solid substance is suspended in a known salt content. This suspension is lyophilized. If the solid substance is washed in several steps, the suspension formed directly with the last wash can be lyophilized; the quantity and salt content of the wash (buffer solution) has to be known naturally in this case, too.

The thus-prepared stable, solid receptor preparation can be used as follows for the quantitative determination of substances able to bind to cerebral receptors:

The suspension of the receptor preparation prepared with an aqueous buffer solution or distilled water of a pH value between 6 and 8 is added to the aqueous solution containing the substance to be examined and labelled with radioactive substance (usually tritium). The mixture is incubated, the solid substance is filtered off, washed with a buffer solution and the radioactivity of the solid substance is determined. Then a known quantity of the non-radioactive substance to be examined is added to the receptor preparation carrying the radioactively labelled substance, the mixture is incubated, the solid substance is filtered off, washed with a buffer solution and its radioactivity is measured again. The latter operation is repeated several times using different quantities of non-radioactive substance to be examined. On the basis of the measurement of radioactivities a concentration/radioactivity calibration line is drawn (the indication "concentration" means the concentration of the non-radioactive substance to be examined).

The quantity of the substance to be examined from body fluids (e.g. spinal fluid) is determined with the help of the calibration line put down as described above in such a way that a known quantity of body fluid is added to the receptor preparation carrying the radioactively labelled substance to be examined, the mixture is incubated, the solid substance is filtered off, washed, its radioactivity is measured, and the concentration belonging to the measured value is read from the calibration line.

The invention is illustrated in detail by the following non-limiting examples.

EXAMPLE 1

Preparation of a receptor preparation

Male rats of strain CFY are decapitated. Their brain is immediately removed and washed with icy physiological salt solution. The brain region called bridge and the medulla oblongata are removed, and from the residue a homogenizate is prepared with a 0.32 molar aqueous saccharose solution of fifteenfold volume. The homogenizate is centrifuged at an acceleration of 1000 g for 10 minutes, then the supernatant is isolated and centrifuged at an acceleration of 20,000 g for 10 minutes. The isolated solid substance is rehomogenized in a fifteenfold volume of cold (+4° C.) distilled water, then the homogenizate is centrifuged at an acceleration of 8000 g for 10 minutes. The supernatant is isolated and centrifuged at an acceleration of 40,000 g for 20 minutes. The obtained solid substance is homogenized in a fiftyfold volume of a 50 mmolar tris-citrate buffer solution (pH=7.1) and the suspension is centrifuged again at an acceleration of 40,000 g. The latter washing step is repeated. Then the solid substance is suspended in a tenfold volume of buffer solution, thereafter it is frozen and stored at a temperature of −20° C. for 10 hours. The suspension is thawed, diluted with distilled water to its fivefold volume and again centrifuged at an acceleration of 40,000 g. This cycle of freezing, thawing and centrifuging is repeated three times. After the last thawing the suspension is divided into parts and is frozen and lyophilized. A powdery receptor preparation is obtained which is admixed with a buffer solution or distilled water before use (measurement). The powdery receptor preparation can be stored for years without any change.

EXAMPLE 2

Taking up of a calibration curve for radioreceptor test

For taking up the calibration curve solutions and suspensions, respectively, of the following compositions are used:

solution I.a: 0.7435 g of NaCl, 0.0186 g of KCl, 0.0144 g of $CaCl_2$, 0.012 g of $MgSO_4$ dissolved in 100 ml of twice distilled water solution I.b: 1 g of bovine serum albumine dissolved in 10 ml of solution I.a solution II.a: 1 mg γ-amino-butyric acid dissolved in 1000 μl of solution V solution II.b: a mixture of 10 μl of solution II.a and 10 ml of solution V solution II.c: a mixture of 100 μl of solution II.b and 900 μl of solution V solution II.d: a mixture of 750 μl of solution II.c and 250 μl of solution V solution II.e: a mixture of 500 μl of solution II.c and 500 μl of solution V solution II.f: a mixture of 250 μl of solution II.c and 750 μl of solution V solution II.g: a mixture of 100 μl of solution II.c and 900 μl of solution V suspension III: 0.2 g of the receptor preparation prepared according to Example 1 is suspended in 3 ml of bi-distilled water, then the suspension is diluted with 17 ml of solution V solution IV: $^3H$-γ-amino-butyric acid solution with an activity of 40 nCi/500 μl (solvent: an aqueous hydrochloric acid solution of pH 4)

solution V: 50 mmolar tris-citrate buffer solution (pH=7.1)

(a) Determination of the total binding capacity (value $C_t$)

The following solutions and suspensions, respectively, are admixed one after the other:

500 μl of solution IV,

10 μl of solution I.b,
10 μl of solution V and
500 μl of suspension III.

The mixture is incubated for 20 minutes at 4° C., then the solid substance is filtered through a microporous Whatman glass filter GF/C. The solid substance is admixed with 10 ml of a liquid scintillation measuring solution of known composition, the suspension is allowed to stand in a refrigerator for 1 hour, then it is shaken and the radioactivity of the suspension is determined. The thus-obtained radioactivity-value is indicated by $C_t$; this is the total quantity of γ-amino-butyric acid which can be bound by the preparation.

(b) Displacing of the radioactively labelled γ-amino-butyric acid with non-radioactive γ-amino-butyric acid (determination of the $C_x$-values)

One proceeds as in paragraph (a) but instead of 10 μl of solution V successively 10 μl each of solutions II.c, II.d, II.e, II.f and II.g, respectively, are used. The measured radioactivity values are indicate by $C_x$.

(c) Determination of the quantity of non-specifically bound γ-amino-butyric acid (value $C_b$)

One proceeds as in paragraph (a) but instead of 10 μl of solution V 10 μl of solution II.a are used. In this case the entire quantity of the specifically bound $^3H$-γ-amino-butyric acid is displaced with non-radioactive γ-amino-butyric acid. On measuring the radioactivity of the sample a correction factor is obtained which characterizes the quantity of the $^3H$-γ-amino-butyric acid non-specifically bound to the preparation. This correction value (value $C_b$) is substracted from values $C_t$ and $C_x$ (see Table 1).

The experimental results are given in Table 1.

TABLE 1

| Solution | Concentration of the inactive γ-amino-butyric acid nM | Count dpm | $\frac{C_t - C_b}{C_x - C_b}$ |
|---|---|---|---|
| II.a | $10^5$ | 160 | — |
| II.c | 10 | 2049 | 2.15 |
| II.d | 7.5 | 2367 | 1.84 |
| II.e | 5.0 | 2780 | 1.55 |
| II.f | 2.5 | 3284 | 1.30 |
| II.g | 1.0 | 3754 | 1.13 |
| V. | — | 4221 | 1.00 |

The values $(C_t - C_b)/(C_x - C_b)$ are plotted against the concentration of the inactive γ-amino-butyric acid and thus a calibration line is obtained.

When the concentration of the γ-amino-butyric acid of a body fluid has to be determined, one proceeds as follows: instead of 10 μl of buffer solution (solution V) or inactive γ-amino-butyric acid solution of known concentration, 10 μl of body fluid are added to the mixture, then the radioactivity of the preparation is measured [see paragraph (a)], and from the calibration line the γ-amino-butyric acid concentration belonging to the measured radioactivity is read.

EXAMPLE 3

Quantitative determination of other substances able to bind specifically to cerebral receptors 3.1
Determination of $^3H$-diazepam 5 mg of the lyophilized receptor preparation prepared according to Example 1 are suspended in the mixture of 0.9 ml of aqueous tris-citrate buffer solution (pH=7.1) and 0.1 ml of bi-distilled water. $^3H$-diazepam is added to the suspension, to have a final concentration of 2 nM, and after incubation at 4° C. for 30 minutes the solid substance is filtered through a microporous Whatman glass filter GF/C aand washed eight times with 2.5 ml of icy tris-citrate buffer solution. The radioactivity is measured as described in Example 2. Thus the total binding capacity of the preparation ($C_t$) is determined. The calibration line is taken up by the method of displacement described in Example 2, and the quantity of the non-specifically bound $^3H$-diazepam (correction factor, $C_b$) is determined as described in Example 2.

3.2. Determination of $^3H$-diazepam binding on γ-amino-butyric acid

One proceeds as in Example 3.1 but $2 \times 10^{-5}$ moles of γ-amino-butyric acid, too, are added to the incubation mixture.

3.3. Determination of $^3H$-γ-amino-butyric acid binding on $Ca^{2+}$ 5 mg of the lyophilized receptor preparation prepared according to Example 1 are suspended in a mixture of 0.9 ml of tris-HCl-buffer solution (pH=7.4) and 0.1 ml of bi-distilled water. 250 μm of calcium-chloride, 40 μm of isoguvacine and 5.4 nM of $^3H$-γ-amino-butyric acid are added to the suspension. The mixture is incubated at room temperature for 30 minutes, then the solid substance is filtered off and washed at room temperature with tris-HCl-buffer solution (pH=7.4). The radioactivity is measured as described in Example 2; the correction factor ($C_b$) is determined by the method described in Example 2.

3.4. Determination of $^3H$-dihydroalprenolol 5 mg of the lyophilized receptor preparation prepared according to Example 1 are suspended in 1 ml of tris-HCl-buffer solution (pH=8.0). 2 nM of $^3H$-dihydroalprenolol are added to the suspension, and after incubating at room temperature for 30 minutes the solid substance is filtered off and washed at room temperature with tris-HCl-buffer solution (pH=8.0). The radioactivity is measured as described in Example 2; the correction factor ($C_b$) is determined as described in Example 2.

The quantity of the specifically bound $^3H$-ligands ($C_t - C_b$) is given in Table 2.

TABLE 2

| Number of the example | Specifically bound $^3H$—ligand fmole/ml |
|---|---|
| 3.1 | 111 |
| 3.2 | 231 |
| 3.3 | 22 |
| 3.4 | 19 |

We claim:
1. A process for preparing a stable receptor preparation suitable for the quantitative determination of substances able to bind to cerebral receptors which comprises: homogenizing a brain or brain-region material with an aqueous solution of an inert substance soluble in water; centrifuging the formed homogenizate at an acceleration of 800 to 110. g for 8 to 20 minutes to form a supernatant; isolating the material from the supernatant by centrifuging the supernatant at an acceleration of 18,00 to 22,000 g for 10 to 20 minutes, the thus-obtained solid substance is rehomogenized in distilled water, the homogenizate is frozen and then thawed and thereafter centrifuged at an acceleration of 7000 to 9000 g for 5–15 minutes, the supernatant is isolated, centrifuged at an acceleration of 35,000 to 45,000 g for 20 to 30 minutes, the obtained solid substance is washed with an aqueous buffer solution of a pH value between 6 and 8, and a suspension consisting of the solid substance and the washing liquid is frozen and then thawed at least once and thereafter the suspension is lyophilized.

2. The process of claim 1, wherein the rehomogenization is carried out in distilled water at a temperature of 4° to 10° C.

3. The process of claim 2, in which 10 to 20 parts by volume of distilled water, per to 1 part by volume of solid substance, are used for the rehomogenization.

4. The process of claim 1, in which a tris-citrate-buffer solution (pH=7.1) is used for the washing.

5. A receptor preparation prepared according to claim 1.

6. A receptor preparation prepared by the process of claim 2.

7. A receptor preparation prepared by the process of claim 3.

8. A receptor preparation prepared by the process of claim 4.

* * * * *

UNITED STATES PATENT AND TRADEMARK OFFICE
CERTIFICATE OF CORRECTION

PATENT NO. : 4,528,131
DATED : July 9, 1985
INVENTOR(S) : Julianna Kardos et al.

It is certified that error appears in the above-identified patent and that said Letters Patent is hereby corrected as shown below:

Column 6, line 64, "110 g" should read -- 1100 g --.

Column 8, line 2, delete "to".

Signed and Sealed this

Seventeenth Day of June 1986

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,528,131
DATED : July 9, 1985
INVENTOR(S) : Julianna Kardos, Gábor Maksay and Miklós Simonyl It is certified that error appears in the above-identified patent and that said Letters Patent is hereby corrected as shown below:

In "[57] ABSTRACT", line 7, delete "110 g" and substitute --1100 g-- therefor.

Signed and Sealed this

Twenty-sixth Day of August 1986

[SEAL]

Attest:

Attesting Officer

DONALD J. QUIGG

Commissioner of Patents and Trademarks